(12) United States Patent
Kanala et al.

(10) Patent No.: US 11,634,623 B2
(45) Date of Patent: Apr. 25, 2023

(54) QUATERNARY AMMONIUM SALTS FOR CORROSION INHIBITION

(71) Applicant: Hindustan Petroleum Corporation Limited, Bangalore (IN)

(72) Inventors: Raghava Krishna Kanala, Bangalore (IN); Naresh Kottari, Bangalore (IN); Srinivasa Rao Ganagalla, Bangalore (IN); Ramkumar Mangala, Bangalore (IN); Ramachandrarao Bojja, Bangalore (IN); Peddy Venkat Chalapathi Rao, Bangalore (IN); Nettem Venkateswarlu Choudary, Bangalore (IN); Gandham Sriganesh, Bangalore (IN)

(73) Assignee: Hindustan Petroleum Corporation Limited, Bangalore (IN)

( * ) Notice: Subject to any disclaimer, the term of this patent is extended or adjusted under 35 U.S.C. 154(b) by 377 days.

(21) Appl. No.: 16/954,475

(22) PCT Filed: Aug. 8, 2019

(86) PCT No.: PCT/IN2019/050583
§ 371 (c)(1),
(2) Date: Jun. 16, 2020

(87) PCT Pub. No.: WO2020/031208
PCT Pub. Date: Feb. 13, 2020

(65) Prior Publication Data
US 2021/0163812 A1    Jun. 3, 2021

(30) Foreign Application Priority Data
Aug. 10, 2018  (IN) .............................. 201841030224

(51) Int. Cl.
| | |
|---|---|
| *C09K 8/54* | (2006.01) |
| *C07C 209/12* | (2006.01) |
| *C07C 211/63* | (2006.01) |
| *C10G 75/02* | (2006.01) |
| *C23F 11/14* | (2006.01) |

(52) U.S. Cl.
CPC .............. *C09K 8/54* (2013.01); *C07C 209/12* (2013.01); *C07C 211/63* (2013.01); *C10G 75/02* (2013.01); *C23F 11/143* (2013.01); *C09K 2208/32* (2013.01)

(58) Field of Classification Search
CPC .............................. C09K 8/54; C09K 2208/32
See application file for complete search history.

(56) References Cited

U.S. PATENT DOCUMENTS

| | | | |
|---|---|---|---|
| 3,349,032 A * | 10/1967 | Krieg .................... | C09K 8/607 166/275 |
| 3,959,158 A | 5/1976 | Stanford et al. | |
| 4,057,390 A | 11/1977 | Quinlan | |
| 5,322,630 A | 6/1994 | Williams et al. | |
| 5,697,443 A * | 12/1997 | Brezinski ............... | C23F 11/04 166/307 |
| 6,265,360 B1 * | 7/2001 | DeTar .................. | C10L 1/1966 508/374 |
| 2004/0144957 A1 * | 7/2004 | Miksic .................... | C09K 8/54 252/391 |
| 2006/0013798 A1 | 1/2006 | Henry et al. | |
| 2013/0228095 A1 | 9/2013 | Miles et al. | |
| 2014/0342953 A1 * | 11/2014 | Reyes ..................... | C09K 8/74 507/240 |
| 2014/0371495 A1 | 12/2014 | Anderson et al. | |
| 2017/0190952 A1 | 7/2017 | Qu et al. | |

FOREIGN PATENT DOCUMENTS

| | | | |
|---|---|---|---|
| CN | 102452946 A | * | 5/2012 |
| CN | 106190078 A | | 12/2016 |

OTHER PUBLICATIONS

English translation of CN102452946A, 7 pages, printed Jul. 1, 2022 (Year: 2022).*
English Translation of CN 106190078A printed Feb. 10, 2023 (Year: 2023).*
International Search Report and Written Opinion for Application No. PCT/IN2019/050583, dated Oct. 29, 2019.
Examination Report for Indian Application No. 201841030224, dated Oct. 3, 2020.

* cited by examiner

*Primary Examiner* — Alicia Bland
(74) *Attorney, Agent, or Firm* — Marshall, Gerstein & Borun LLP

(57) ABSTRACT

The present disclosure provides a bis-quaternary ammonium salt of Formula I $$X^\ominus \quad R_1\underset{R_2}{\overset{\oplus}{N}}\text{-}(CH_2)_n\text{-}A\text{-}(CH_2)_m\text{-}\underset{R_1}{\overset{\oplus}{N}}\text{-}R_3 \quad X^\ominus \quad R_2,$$

Formula I wherein A is selected from O, NH, S, C(O), C(NH) or C(S); $R_1$ and $R_2$ are independently selected from $C_{1-3}$ alkyl or H; $R_3$ is $C_{1-16}$ alkyl, $C_{13-20}$ aralkyl or $C_{2-16}$ allyl; $X^-$ is selected from chloro, bromo, iodo, hydroxide, nitrate or sulphate; and n and m are independently 1 to 6. Furthermore, a corrosion inhibition formulation comprising said bis-quaternary ammonium salt is revealed. Also, convenient processes for the preparation of the salt of Formula I and the formulation are provided.

12 Claims, No Drawings

QUATERNARY AMMONIUM SALTS FOR CORROSION INHIBITION

TECHNICAL FIELD OF THE INVENTION

The present invention relates to a corrosion inhibitor composition that prevents or retards corrosion of metal surfaces. In particular, the invention relates to a novel corrosion inhibitor formulation comprising quaternary ammonium salt that prevents internal corrosion of metallurgies such as carbon steel, stainless steel, copper, brass, lead, and zinc involved in fuel storage and transportation through pipelines.

BACKGROUND OF THE INVENTION

Steel, which is an alloy of carbon and iron has been the backbone of the modern industrialized world. Mild steel (a type of carbon steel), the most common form of steel, typically comprises about 0.05-0.25% carbon. The introduction of carbon content is particularly important in providing it necessary processing. Though steel is extensively used, tackling corrosion of steel remains a challenge. This is particularly true for a tropical country like India, where environmental factors such as humidity contribute to accelerated corrosion.

Carbon steel is a common construction material in oilfield facilities due to lower cost than corrosion resistant alloys (CRAs), but with a poor corrosion resistance. Controlling internal corrosion is the main problem encountered in flowlines and pipelines made from carbon steel. The corrosion process is primarily associated with the presence of free water in offshore or onshore production facilities, particularly when it is accompanied by carbon dioxide gas. Additionally, internal corrosion is usually associated with significant partial pressures of $CO_2$ and/or $H_2S$ in the pipelines. Thus, corrosion inhibitor injection in oilfields is a very common and useful method for pipeline internal corrosion prevention.

A variety of corrosion inhibitors have been used with the gas transmission pipelines to inhibit such corrosion in the metallurgy during storage, pipeline transportation. A key criterion for selection of inhibitors is the solubility in hydrocarbon oil/gas. Fatty acid amines have been attempted for the purpose (U.S. Pat. Nos. 3,959,158 and 5,322,630). However, along with the suitable oil-solubility, the presence of polar groups has been identified as essential in inhibiting corrosion. An example is the success of ionic liquids as corrosion inhibitors (US20140371495).

However, because of the diverse conditions that are present inside the industrial equipment, the efficiency of the corrosion inhibitor may vary in the same industrial equipment. An adequate material selection suitable for the operating conditions is essential to find a corrosion resistant material. The effectiveness of a corrosion inhibitor lies in the fact that it must be able to transfer water from the metal surface, interact with anodic and cathodic reaction sites to retard oxidation and reduction corrosion reaction and prevent transportation of water and corrosion active species on metal surface. An additional shortcoming associated with inhibitors used for fuel pipelines, is that they tend to alter the fuel quality, thereby compromising on the standards such as BIS and ASTM.

Therefore, there is a need to develop a corrosion inhibitor which is effective against a wide variety of metallurgies, while being oil-soluble, and also being effective in a broad temperature and moisture range.

SUMMARY OF THE INVENTION

In an aspect of the present disclosure, there is provided a bis-quaternary ammonium salt of Formula I

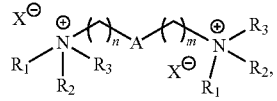

Formula I wherein A is selected from O, NH, S, C(O), C(NH) or C(S); $R_1$ and $R_2$ are independently selected from $C_{1-3}$ alkyl or H; $R_3$ is $C_{1-16}$ alkyl, $C_{13-20}$ aralkyl or $C_{2-16}$ allyl; $X^-$ is selected from chloro, bromo, iodo, hydroxide, nitrate or sulphate; and n and m are independently 1 to 6.

In an aspect of the present disclosure, there is provided a corrosion inhibitor formulation comprising: a) the bis-quaternary ammonium salt of Formula I

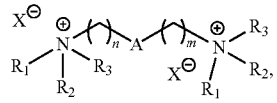

Formula I wherein A is selected from O, NH, S, C(O), C(NH) or C(S); $R_1$ and $R_2$ are independently selected from $C_{1-3}$ alkyl or H; $R_3$ is $C_{1-16}$ alkyl, $C_{13-20}$ aralkyl or $C_{2-16}$ allyl; $X^-$ is selected from chloro, bromo, iodo, hydroxide, nitrate or sulphate; and n and m are independently 1 to 6; b) alkyldimethylbenzylammonium chloride; c) at least one fatty acid methyl ester; d) at least one viscosity reducing agent; and e) at least one solubilizing agent, wherein the bis-quaternary ammonium salt of Formula I to the at least one fatty acid methyl ester weight ratio is in a range of 1:3.7-1:5.7.

In another aspect of the present disclosure, there is provided a process for preparation of the bis-quaternary ammonium salt of Formula I, said process comprising: a) obtaining at least one alkyl halide; b) obtaining at least one amine; c) contacting the at least one alkyl halide and at least one amine in the presence of at least one solvent to obtain the bis-quaternary ammonium salt of Formula I.

In an aspect of the present disclosure, there is provided a process for the preparation of the corrosion inhibitor formulation comprising: a) the bis-quaternary ammonium salt of Formula I; b) alkyldimethylbenzylammonium chloride; c) at least one fatty acid methyl ester; d) at least one viscosity reducing agent; and e) at least one solubilizing agent, wherein the bis-quaternary ammonium salt of Formula I to the at least one fatty acid methyl ester weight ratio is in a range of 1:3.7-1:5.7, said process comprising: a) obtaining bis-quaternary ammonium salt of Formula I by the process comprising: i) obtaining at least one alkyl halide; ii) obtaining at least one amine; iii) contacting the at least one alkyl halide and at least one amine in the presence of at least one solvent to obtain the bis-quaternary ammonium salt; b) obtaining the alkyldimethylbenzylammonium chloride; c) obtaining the at least one fatty acid methyl ester; d) obtaining the at least one viscosity reducing agent; e) obtaining the at least one solubilizing agent; and f) contacting the bis-quaternary ammonium salt of Formula I, alkyldimethylbenzylammonium chloride, the at least one fatty acid methyl ester, the at least one solubilizing agent, and the at least one viscosity reducing agent to obtain the corrosion inhibitor formulation.

These and other features, aspects and advantages of the present subject matter will be better understood with reference to the following description and appended claims. This summary is provided to introduce a selection of concepts in a simplified form. This summary is not intended to identify key features or essential features of the claimed subject matter, nor is it intended to be used to limit the scope of the claimed subject matter.

DETAILED DESCRIPTION

Those skilled in the art will be aware that the present disclosure is subject to variations and modifications other than those specifically described. It is to be understood that the present disclosure includes all such variations and modifications. The disclosure also includes all such steps, features, compositions and compounds referred to or indicated in this specification, individually or collectively and any and all combinations of any or more of such steps or features.

Definitions

For convenience, before further description of the present disclosure, certain terms employed in the specification, and examples are collected here. These definitions should be read in the light of the remainder of the disclosure and understood as by a person of skill in the art. The terms used herein have the meanings recognized and known to those of skill in the art, however, for convenience and completeness, particular terms and their meanings are set forth below.

The articles "a", "an" and "the" are used to refer to one or to more than one (i.e., to at least one) of the grammatical object of the article.

The terms "comprise" and "comprising" are used in the inclusive, open sense, meaning that additional elements may be included. Throughout this specification, unless the context requires otherwise the word "comprise", and variations, such as "comprises" and "comprising", will be understood to imply the inclusion of a stated element or step or group of element or steps but not the exclusion of any other element or step or group of element or steps.

The term "including" is used to mean "including but not limited to". "Including" and "including but not limited to" are used interchangeably.

Ratios, concentrations, amounts, and other numerical data may be presented herein in a range format. It is to be understood that such range format is used merely for convenience and brevity and should be interpreted flexibly to include not only the numerical values explicitly recited as the limits of the range, but also to include all the individual numerical values or sub-ranges encompassed within that range as if each numerical value and sub-range is explicitly recited. For example, a temperature range of about 0° C. to about 100° C. should be interpreted to include not only the explicitly recited limits of about 0° C. to about 100° C., but also to include sub-ranges, such as 2° C. to 100° C., 0° C. to 95° C., and so forth, as well as individual amounts, including fractional amounts, within the specified ranges, such as 0.2° C., 40.6° C., and 98.3° C., for example.

The term "oil-soluble" or "hydrocarbon-soluble" is used to refer to the compounds that are essentially dissolved or completely dissociated from other compounds or molecules in an oil or hydrocarbon feedstock.

The term "steel" refers to an alloy of iron, mainly comprising varying amounts of carbon and other metals. The corrosion inhibitor formulation as described by the present disclosure is effective on a range of metallurgies including mild steel, carbon steel, stainless steel, among others.

The term "oil" or "fuel" or hydrocarbon" are used in the present disclosure interchangeably to refer to hydrocarbon fuel such as liquefied petroleum gas that are extracted from remote sources and transported via pipelines.

The term "alkyl" refers to a saturated hydrocarbon chain having the specified number of carbon atoms. For example, which are not limited, $C_{1-16}$ alkyl refers to an alkyl group having from 1-16 carbon atoms. Alkyl groups may be straight or branched chained groups. Representative branched alkyl groups have one, two, or three branches. Preferred alkyl groups include, without limitation, methyl, ethyl, n-propyl, isopropyl, butyl, pentyl, hexyl, decyl, and dodecyl.

The term "aralkyl" refers to an aromatic hydrocarbon chain having the specified number of carbon atoms. For example, which are not limited, $C_{13-20}$ aralkyl refers to an alkyl group further substituted with an aryl group, in total having 1-16 carbon atoms. Preferred aralkyl groups include, without limitation, —$CH_2C_6H_5$ or benzyl, —$C_2H_5C_6H_5$ and —$C_3H_7C_6H_5$.

The term "allyl" refers to an unsaturated hydrocarbon chain having the specified number of carbon atoms. An allyl group comprises methylene bridge attached to a vinyl group. For example, which are not limited, $C_{2-16}$ allyl refers to methylene group further substituted with an unsaturated hydrocarbon having 1-15 carbon atoms. Preferred allyl groups include, without limitation, prop-2-en-1-yl, crotonyl and butan-2-en-1-yl.

The present disclosure is not to be limited in scope by the specific embodiments described herein, which are intended for the purposes of exemplification only. Functionally equivalent products, compositions, and methods are clearly within scope of the disclosure, as described herein.

As described in the background section, there is need for an oil-soluble corrosion inhibitor formulation that is able to efficiently mitigate corrosion without altering the quality of the hydrocarbon fuel or oil. In accordance with the same, a bis-quaternary ammonium salt has been provided which can effectively be used as part of corrosion inhibition formulation. The formulation is found to be effective in reducing corrosion rate and enhancing corrosion inhibition.

In an embodiment of the present disclosure, there is provided a bis-quaternary ammonium salt of Formula I

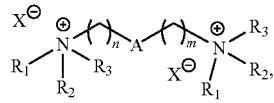

Formula I wherein A is selected from O, NH, S, C(O), C(NH) or C(S); $R_1$ and $R_2$ are independently selected from $C_{1-3}$ alkyl or H; $R_3$ is $C_{1-16}$ alkyl, $C_{13-20}$ aralkyl or $C_{2-16}$ allyl; $X^-$ is selected from chloro, bromo, iodo, hydroxide, nitrate or sulphate; and n and m are independently 1 to 6. In another embodiment of the present disclosure, A is selected from O, NH, S, C(O), C(NH) or C(S); $R_1$ and $R_2$ are independently selected from $C_1$ alkyl or H; $R_3$ is $C_{1-12}$ alkyl; $X^-$ is selected from chloro, bromo, iodo, hydroxide, nitrate or sulphate; and n and m are independently 1 to 3.

In an embodiment of the present disclosure, there is provided a bis-quaternary ammonium salt of Formula I

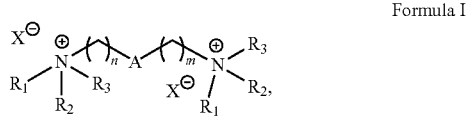

Formula I wherein A is C(O); $R_1$ and $R_2$ are $C_1$ alkyl; $R_3$ is $C_{12}$ alkyl; $X^-$ is chloro; and n and m is 1.

In an embodiment of the present disclosure, there is provided a bis-quaternary ammonium salt of Formula I

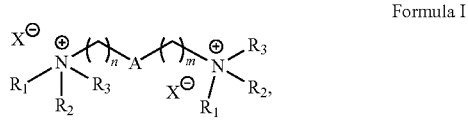

Formula I wherein A is selected from O, NH or S; $R_1$ and $R_2$ are H; $R_3$ is $C_{1-16}$ alkyl, $C_{13-20}$ aralkyl or $C_{2-16}$ allyl; $X^-$ is chloro; and n and m is 3.

In an embodiment of the present disclosure, there is provided a bis-quaternary ammonium salt of Formula I as described herein, wherein $R_1$ and $R_2$ are independently selected from $C_1$ alkyl or H; $R_3$ is $C_{1-14}$ alkyl; X is chloro; and n and m are independently 1 to 4.

In an embodiment of the present disclosure, there is provided a corrosion inhibitor formulation comprising: a) the bis-quaternary ammonium salt of Formula I

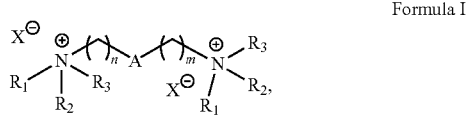

Formula I wherein A is selected from O, NH, S, C(O), C(NH) or C(S); $R_1$ and $R_2$ are independently selected from $C_{1-3}$ alkyl or H; $R_3$ is $C_{1-16}$ alkyl, $C_{13-20}$ aralkyl or $C_{2-16}$ allyl; $X^-$ is selected from chloro, bromo, iodo, hydroxide, nitrate or sulphate; and n and m are independently 1 to 6; b) alkyldimethylbenzylammonium chloride; c) at least one fatty acid methyl ester; d) at least one viscosity reducing agent; and e) at least one solubilizing agent, wherein the bis-quaternary ammonium salt of Formula I to the at least one fatty acid methyl ester weight ratio is in a range of 1:3.7-1:5.7. In another embodiment of the present disclosure, wherein the bis-quaternary ammonium salt of Formula I to the at least one fatty acid methyl ester weight ratio is in a range of 1:4-1:5. In yet another embodiment of the present disclosure, wherein the bis-quaternary ammonium salt of Formula I to the at least one fatty acid methyl ester weight ratio is 1:4.7.

In an embodiment of the present disclosure, there is provided a corrosion inhibitor formulation as described herein, wherein alkyldimethylbenzylammonium chloride is selected from dodecyldimethylbenzylammonium chloride, tetradecyldimethylbenzylammonium chloride, or hexadecyldimethylbenzylammonium chloride. In another embodiment of the present disclosure, the alkyldimethylbenzylammonium chloride has an alkyl group selected from $C_{1-16}$ alkyl.

In an embodiment of the present disclosure, there is provided a corrosion inhibitor formulation comprising: a) the bis-quaternary ammonium salt of Formula I

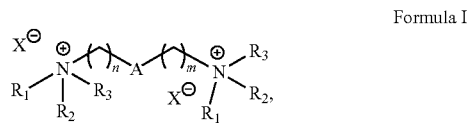

Formula I wherein A is selected from O, NH, S, C(O), C(NH) or C(S); $R_1$ and $R_2$ are independently selected from $C_1$ alkyl or H; $R_3$ is $C_{1-14}$ alkyl; X is chloro; and n and m are independently 1 to 4; b) alkyldimethylbenzylammonium chloride; c) at least one fatty acid methyl ester; d) at least one viscosity reducing agent; and e) at least one solubilizing agent, wherein the bis-quaternary ammonium salt of Formula I to the at least one fatty acid methyl ester weight ratio is in a range of 1:3.7-1:5.7.

In an embodiment of the present disclosure, there is provided a corrosion inhibitor formulation as described herein, wherein the bis-quaternary ammonium salt of Formula I to the alkyldimethylbenzylammonium chloride weight ratio is in a range of 1:3-1:5. In another embodiment of the present disclosure, the alkyldimethylbenzylammonium chloride weight ratio is in a range of 1:3.5-1:4.5. In yet another embodiment of the present disclosure, the alkyldimethylbenzylammonium chloride weight ratio is 1:4.

In an embodiment of the present disclosure, there is provided a corrosion inhibitor formulation as described herein, wherein the formulation comprising: a) the bis-quaternary ammonium salt of Formula I; b) alkyldimethylbenzylammonium chloride; c) at least one fatty acid methyl ester; d) at least one viscosity reducing agent; and e) at least one solubilizing agent, wherein the bis-quaternary ammonium salt of Formula I to the at least one fatty acid methyl ester weight ratio is in a range of 1:3.7-1:5.7 and the bis-quaternary ammonium salt of Formula I to the alkyldimethylbenzylammonium chloride weight ratio is in a range of 1:3-1:5.

In an embodiment of the present disclosure, there is provided a corrosion inhibitor formulation as described herein, wherein the at least one fatty acid methyl ester is selected from the group consisting of soyabean oil methyl ester, bio-oil derived fatty acid methyl ester, palmitic acid methyl ester, stearic acid methyl ester, oleic acid methyl ester, linoleic acid methyl ester, rapeseed oil methyl ester, and combinations thereof. In another embodiment of the present disclosure, fatty acid methyl ester is soyabean oil methyl ester. In yet another embodiment of the present disclosure, the fatty acid methyl ester is bio-oil fatty acid ester selected from sunflower oil methyl ester or castor oil methyl ester.

In an embodiment of the present disclosure, there is provided a corrosion inhibitor formulation as described herein, wherein the formulation comprising: a) the bis-quaternary ammonium salt of Formula I; b) alkyldimethylbenzylammonium chloride; c) at least one fatty acid methyl ester; d) at least one viscosity reducing agent; and e) at least one solubilizing agent, wherein the bis-quaternary ammonium salt of Formula I to the at least one fatty acid methyl ester weight ratio is in a range of 1:3.7-1:5.7 and the at least one fatty acid methyl ester is selected from the group consisting of soyabean oil methyl ester, bio-oil derived fatty acid methyl ester, palmitic acid methyl ester, stearic acid methyl ester, oleic acid methyl ester, linoleic acid methyl ester, rapeseed oil methyl ester, and combinations thereof.

In an embodiment of the present disclosure, there is provided a corrosion inhibitor formulation as described herein, wherein the formulation comprising: a) the bis-quaternary ammonium salt of Formula I; b) alkyldimethylbenzylammonium chloride; c) at least one fatty acid methyl ester; d) at least one viscosity reducing agent; and e) at least one solubilizing agent, wherein the bis-quaternary ammonium salt of Formula I to the at least one fatty acid methyl ester weight ratio is in a range of 1:3.7-1:5.7, the bis-quaternary ammonium salt of Formula I to the alkyldimethylbenzylammonium chloride weight ratio is in a range of 1:3-1:5 and the at least one fatty acid methyl ester is selected from the group consisting of soyabean oil methyl ester, bio-oil derived fatty acid methyl ester, palmitic acid methyl ester, stearic acid methyl ester, oleic acid methyl ester, linoleic acid methyl ester, rapeseed oil methyl ester, and combinations thereof.

In an embodiment of the present disclosure, there is provided a corrosion inhibitor formulation as described herein, wherein the at least one viscosity reducing agent is selected from the group consisting of isopropanol, propanol, ethanol, toluene, benzene, hexane, kerosene, diesel, propargyl alcohol, and combinations thereof. In another embodiment of the present, the at least one viscosity reducing agent is isopropanol.

In an embodiment of the present disclosure, there is provided a corrosion inhibitor formulation as described herein, wherein the formulation comprising: a) the bis-quaternary ammonium salt of Formula I; b) alkyldimethylbenzylammonium chloride; c) at least one fatty acid methyl ester; d) at least one viscosity reducing agent; and e) at least one solubilizing agent, wherein the bis-quaternary ammonium salt of Formula I to the at least one fatty acid methyl ester weight ratio is in a range of 1:3.7-1:5.7 and the at least one viscosity reducing agent is selected from the group consisting of isopropanol, propanol, ethanol, toluene, benzene, hexane, kerosene, diesel, propargyl alcohol, and combinations thereof.

In an embodiment of the present disclosure, there is provided a corrosion inhibitor formulation as described herein, wherein the formulation comprising: a) the bis-quaternary ammonium salt of Formula I; b) alkyldimethylbenzylammonium chloride; c) at least one fatty acid methyl ester; d) at least one viscosity reducing agent; and e) at least one solubilizing agent, wherein the bis-quaternary ammonium salt of Formula I to the at least one fatty acid methyl ester weight ratio is in a range of 1:3.7-1:5.7, the bis-quaternary ammonium salt of Formula I to the alkyldimethylbenzylammonium chloride weight ratio is in a range of 1:3-1:5 and the at least one viscosity reducing agent is selected from the group consisting of isopropanol, propanol, ethanol, toluene, benzene, hexane, kerosene, diesel, propargyl alcohol, and combinations thereof.

In an embodiment of the present disclosure, there is provided a corrosion inhibitor formulation as described herein, wherein the formulation comprising: a) the bis-quaternary ammonium salt of Formula I; b) alkyldimethylbenzylammonium chloride; c) at least one fatty acid methyl ester; d) at least one viscosity reducing agent; and e) at least one solubilizing agent, wherein the bis-quaternary ammonium salt of Formula I to the at least one fatty acid methyl ester weight ratio is in a range of 1:3.7-1:5.7, the bis-quaternary ammonium salt of Formula I to the alkyldimethylbenzylammonium chloride weight ratio is in a range of 1:3-1:5, the at least one fatty acid methyl ester is selected from the group consisting of soyabean oil methyl ester, bio-oil derived fatty acid methyl ester, palmitic acid methyl ester, stearic acid methyl ester, oleic acid methyl ester, linoleic acid methyl ester, rapeseed oil methyl ester, and combinations thereof and the at least one viscosity reducing agent is selected from the group consisting of isopropanol, propanol, ethanol, toluene, benzene, hexane, kerosene, diesel, propargyl alcohol, and combinations thereof.

In an embodiment of the present disclosure, there is provided a corrosion inhibitor formulation as described herein, wherein the at least one solubilizing agent is selected from the group consisting of acetic acid, hydroxyacetic acid, tannic acid, 2,6-pyridine dicarboxylic acid, lactic acid, glucono 6-lactone (gluconic acid), 2-puroic acid, thiophene-2-carboxylic acid, 2,3-pyridine dicarboxylic acid, phosphonoacetic acid, thiophene-2-acetic acid, mercapto acetic acid, propionic acid, butanoic acid, pentanoic acid, benzoic acid, and combinations thereof. In another embodiment of the present disclosure, the at least one solubilizing agent is acetic acid.

In an embodiment of the present disclosure, there is provided a corrosion inhibitor formulation as described herein, wherein the formulation comprising: a) the bis-quaternary ammonium salt of Formula I; b) alkyldimethylbenzylammonium chloride; c) at least one fatty acid methyl ester; d) at least one viscosity reducing agent; and e) at least one solubilizing agent, wherein the bis-quaternary ammonium salt of Formula I to the at least one fatty acid methyl ester weight ratio is in a range of 1:3.7-1:5.7 and the at least one solubilizing agent is selected from the group consisting of acetic acid, hydroxyacetic acid, tannic acid, 2,6-pyridine dicarboxylic acid, lactic acid, glucono 6-lactone (gluconic acid), 2-puroic acid, thiophene-2-carboxylic acid, 2,3-pyridine dicarboxylic acid, phosphonoacetic acid, thiophene-2-acetic acid, mercapto acetic acid, propionic acid, butanoic acid, pentanoic acid, benzoic acid, and combinations thereof.

In an embodiment of the present disclosure, there is provided a corrosion inhibitor formulation as described herein, wherein the formulation comprising: a) the bis-quaternary ammonium salt of Formula I; b) alkyldimethylbenzylammonium chloride; c) at least one fatty acid methyl ester; d) at least one viscosity reducing agent; and e) at least one solubilizing agent, wherein the bis-quaternary ammonium salt of Formula I to the at least one fatty acid methyl ester weight ratio is in a range of 1:3.7-1:5.7, the bis-quaternary ammonium salt of Formula I to the alkyldimethylbenzylammonium chloride weight ratio is in a range of 1:3-1:5 and the at least one solubilizing agent is selected from the group consisting of acetic acid, hydroxyacetic acid, tannic acid, 2,6-pyridine dicarboxylic acid, lactic acid, glucono 6-lactone (gluconic acid), 2-puroic acid, thiophene-2-carboxylic acid, 2,3-pyridine dicarboxylic acid, phosphonoacetic acid, thiophene-2-acetic acid, mercapto acetic acid, propionic acid, butanoic acid, pentanoic acid, benzoic acid, and combinations thereof.

In an embodiment of the present disclosure, there is provided a corrosion inhibitor formulation as described herein, wherein the formulation comprising: a) the bis-quaternary ammonium salt of Formula I; b) alkyldimethylbenzylammonium chloride; c) at least one fatty acid methyl ester; d) at least one viscosity reducing agent; and e) at least one solubilizing agent, wherein the bis-quaternary ammonium salt of Formula I to the at least one fatty acid methyl ester weight ratio is in a range of 1:3.7-1:5.7, the bis-quaternary ammonium salt of Formula I to the alkyldimethylbenzylammonium chloride weight ratio is in a range of 1:3-1:5, the at least one fatty acid methyl ester is selected from the group consisting of soyabean oil methyl ester, bio-oil derived fatty acid methyl ester, palmitic acid methyl ester, stearic acid methyl ester, oleic acid methyl ester, linoleic acid methyl ester, rapeseed oil methyl ester, and combinations thereof, the at least one viscosity reducing agent is selected from the group consisting of isopropanol, propanol, ethanol, toluene, benzene, hexane, kerosene, diesel, propargyl alcohol, and combinations thereof and the at least one solubilizing agent is selected from the group consisting of acetic acid, hydroxyacetic acid, tannic acid, 2,6-pyridine dicarboxylic acid, lactic acid, glucono 6-lactone (gluconic acid), 2-puroic acid, thiophene-2-carboxylic acid, 2,3-pyridine dicarboxylic acid, phosphonoacetic acid, thiophene-2-acetic acid, mercapto acetic acid, propionic acid, butanoic acid, pentanoic acid, benzoic acid, and combinations thereof.

In an embodiment of the present disclosure, there is provided a corrosion inhibitor formulation as described herein, wherein the formulation comprises: a) the bis-quaternary ammonium salt of Formula I having a weight percentage in a range of 8-12% with respect to the formulation; b) alkyldimethylbenzylammonium chloride having a weight percentage in a range of 30-50% with respect to the formulation; c) at least one fatty acid methyl ester having a weight percentage in a range of 37-57% with respect to the formulation; d) at least one viscosity reducing agent having a weight percentage in a range of 0.1-0.8% with respect to the formulation; and e) at least one solubilizing agent having a weight percentage in a range of 1.5-3.5% with respect to the formulation. In another embodiment of the present disclosure, the formulation comprises: a) the bis-quaternary ammonium salt of Formula I having a weight percentage in a range of 8.5-11.5% with respect to the formulation; b) alkyldimethylbenzylammonium chloride having a weight percentage in a range of 35-45% with respect to the formulation; c) at least one fatty acid methyl ester having a weight percentage in a range of 42-52% with respect to the formulation; d) at least one viscosity reducing agent having a weight percentage in a range of 0.2-0.7% with respect to the formulation; and e) at least one solubilizing agent having a weight percentage in a range of 2.0-3.0% with respect to the formulation. In yet another embodiment of the present disclosure, the formulation comprises: a) the bis-quaternary ammonium salt of Formula I having a weight percentage of 10% with respect to the formulation; b) alkyldimethylbenzylammonium chloride having a weight percentage of 40% with respect to the formulation; c) at least one fatty acid methyl ester having a weight percentage of 47% with respect to the formulation; d) at least one viscosity reducing agent having a weight percentage of 0.5% with respect to the formulation; and e) at least one solubilizing agent having a weight percentage of 2.5% with respect to the formulation In an embodiment of the present disclosure, there is provided a corrosion inhibitor formulation as described herein, wherein the formulation comprising: a) the bis-quaternary ammonium salt of Formula I having a weight percentage in a range of 8-12% with respect to the formulation; b) alkyldimethylbenzylammonium chloride having a weight percentage in a range of 30-50% with respect to the formulation; c) at least one fatty acid methyl ester having a weight percentage in a range of 37-57% with respect to the formulation; d) at least one viscosity reducing agent having a weight percentage in a range of 0.1-0.8% with respect to the formulation; and e) at least one solubilizing agent having a weight percentage in a range of 1.5-3.5% with respect to the formulation, wherein the bis-quaternary ammonium salt of Formula I to the at least one fatty acid methyl ester weight ratio is in a range of 1:3.7-1:5.7.

In an embodiment of the present disclosure, there is provided a corrosion inhibitor formulation as described herein, wherein the formulation comprising: a) the bis-quaternary ammonium salt of Formula I having a weight percentage in a range of 8-12% with respect to the formulation; b) alkyldimethylbenzylammonium chloride having a weight percentage in a range of 30-50% with respect to the formulation; c) at least one fatty acid methyl ester having a weight percentage in a range of 37-57% with respect to the formulation; d) at least one viscosity reducing agent having a weight percentage in a range of 0.1-0.8% with respect to the formulation; and e) at least one solubilizing agent having a weight percentage in a range of 1.5-3.5% with respect to the formulation, wherein the bis-quaternary ammonium salt of Formula I to the at least one fatty acid methyl ester weight ratio is in a range of 1:3.7-1:5.7 and the bis-quaternary ammonium salt of Formula I to the alkyldimethylbenzylammonium chloride weight ratio is in a range of 1:3-1:5.

In an embodiment of the present disclosure, there is provided a corrosion inhibitor formulation as described herein, wherein the corrosion inhibitor formulation has a dosage in a range of 10-30 ppm. In another embodiment of the present disclosure, the corrosion inhibitor formulation has a dosage in a range of 15-25 ppm. In another embodiment of the present disclosure, the corrosion inhibitor formulation has a dosage of 20 ppm.

In an embodiment of the present disclosure, there is provided a corrosion inhibitor formulation as described herein, wherein the formulation comprising: a) the bis-quaternary ammonium salt of Formula I having a weight percentage in a range of 8-12% with respect to the formulation; b) alkyldimethylbenzylammonium chloride having a weight percentage in a range of 30-50% with respect to the formulation; c) at least one fatty acid methyl ester having a weight percentage in a range of 37-57% with respect to the formulation; d) at least one viscosity reducing agent having a weight percentage in a range of 0.1-0.8% with respect to the formulation; and e) at least one solubilizing agent having a weight percentage in a range of 1.5-3.5% with respect to the formulation, wherein the bis-quaternary ammonium salt of Formula I to the at least one fatty acid methyl ester weight ratio is in a range of 1:3.7-1:5.7 and the corrosion inhibitor formulation has a dosage in a range of 10-30 ppm.

In an embodiment of the present disclosure, there is provided a corrosion inhibitor formulation as described herein, wherein the formulation comprising: a) the bis-quaternary ammonium salt of Formula I having a weight percentage in a range of 8-12% with respect to the formulation; b) alkyldimethylbenzylammonium chloride having a weight percentage in a range of 30-50% with respect to the formulation; c) at least one fatty acid methyl ester having a weight percentage in a range of 37-57% with respect to the formulation; d) at least one viscosity reducing agent having a weight percentage in a range of 0.1-0.8% with respect to the formulation; and e) at least one solubilizing agent having a weight percentage in a range of 1.5-3.5% with respect to the formulation, wherein the bis-quaternary ammonium salt of Formula I to the at least one fatty acid methyl ester weight ratio is in a range of 1:3.7-1:5.7, the bis-quaternary ammonium salt of Formula I to the alkyldimethylbenzylammonium chloride weight ratio is in a range of 1:3-1:5 and the corrosion inhibitor formulation has a dosage in a range of 10-30 ppm.

In an embodiment of the present disclosure, there is provided a process for preparation of the bis-quaternary ammonium salt of Formula I,

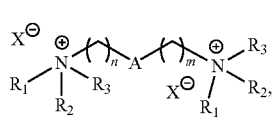

Formula I wherein A is selected from O, NH, S, C(O), C(NH) or C(S); $R_1$ and $R_2$ are independently selected from $C_{1-3}$ alkyl or H; $R_3$ is $C_{1-16}$ alkyl, $C_{13-20}$ aralkyl or $C_{2-16}$ allyl; $X^-$ is selected from chloro, bromo, iodo, hydroxide, nitrate or sulphate; and n and m are independently 1 to 6, said process comprising: a) obtaining at least one alkyl halide; b) obtaining at least one amine; c) contacting the at least one alkyl halide and at least one amine in the presence of at least one solvent to obtain the bis-quaternary ammonium salt of Formula I.

In an embodiment of the present disclosure, there is provided a process for preparation of the bis-quaternary ammonium salt of Formula I,

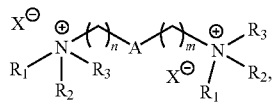

Formula I wherein A is selected from O, NH, S, C(O), C(NH) or C(S); $R_1$ and $R_2$ are independently selected from $C_1$ alkyl or H; $R_3$ is $C_{1-14}$ alkyl; X is chloro; and n and m are independently 1 to 4, said process comprising: a) obtaining at least one alkyl halide; b) obtaining at least one amine; c) contacting the at least one alkyl halide and at least one amine in the presence of at least one solvent to obtain the bis-quaternary ammonium salt of Formula I.

In an embodiment of the present disclosure, there is provided a process for preparation of the bis-quaternary ammonium salt of Formula I as described herein, wherein the at least one alkyl halide is selected from the group consisting of 1,3-dichloroacetone, 1,3-dichloropropan-2-imine, 1,3-dichlorothioacetone, and combinations thereof.

In an embodiment of the present disclosure, there is provided a process for preparation of the bis-quaternary ammonium salt of Formula I as described herein, wherein the at least one amine is selected from the group consisting of N,N-dimethyldodecylamine, 1,3-dichloropropan-2-imine, bis(3-aminopropyl)ether, bis(3-aminopropyl)thioether, N-(3-aminopropyl)-1,3-propanediamine, and combinations thereof. In another embodiment of the present disclosure, the at least one amine is N,N-dimethylalkylamine, wherein alkyl group is selected from $C_{1-21}$ alkyl.

In an embodiment of the present disclosure, there is provided a process for preparation of the bis-quaternary ammonium salt of Formula I as described herein, wherein the at least one solvent is toluene.

In an embodiment of the present disclosure, there is provided a process for preparation of the bis-quaternary ammonium salt of Formula I as described herein, wherein contacting the at least one alkyl halide and at least one amine in the presence of at least one solvent is carried out at a temperature in a range of 0-100° C. for a period in a range of 15-45 minutes to obtain the bis-quaternary ammonium salt of Formula I. In another embodiment of the present disclosure, contacting the at least one alkyl halide and at least one amine in the presence of at least one solvent is carried out at a temperature in a range of 0-35° C. for a period in a range of 20-40 minutes to obtain the bis-quaternary ammonium salt of Formula I. In yet another embodiment of the present disclosure, contacting the at least one alkyl halide and at least one amine in the presence of at least one solvent is carried out at a temperature in a range of 0-25° C. for a period of 30 minutes to obtain the bis-quaternary ammonium salt of Formula I.

In an embodiment of the present disclosure, there is provided a process for preparation of the bis-quaternary ammonium salt of Formula I as described herein, wherein said process comprising: a) obtaining at least one alkyl halide; b) obtaining at least one amine; c) contacting the at least one alkyl halide and at least one amine in the presence of at least one solvent is carried out at a temperature in a range of 0-100° C. for a period in a range of 15-45 minutes to obtain the bis-quaternary ammonium salt of Formula I.

In an embodiment of the present disclosure, there is provided a process for the preparation of the corrosion inhibitor formulation comprising: a) the bis-quaternary ammonium salt of Formula I,

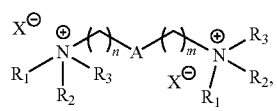

Formula I wherein A is selected from O, NH, S, C(O), C(NH) or C(S); $R_1$ and $R_2$ are independently selected from $C_{1-3}$ alkyl or H; $R_3$ is $C_{1-16}$ alkyl, $C_{13-20}$ aralkyl or $C_{2-16}$ allyl; $X^-$ is selected from chloro, bromo, iodo, hydroxide, nitrate or sulphate; and n and m are independently 1 to 6; b) alkyldimethylbenzylammonium chloride; c) at least one fatty acid methyl ester; d) at least one viscosity reducing agent; and e) at least one solubilizing agent, wherein the bis-quaternary ammonium salt of Formula I to the at least one fatty acid methyl ester weight ratio is in a range of 1:3.7-1:5.7, said process comprising: a) obtaining bis-quaternary ammonium salt of Formula I by the process comprising: i) obtaining at least one alkyl halide; ii) obtaining at least one amine; iii) contacting the at least one alkyl halide and at least one amine in the presence of at least one solvent to obtain the bis-quaternary ammonium salt; b) obtaining the alkyldimethylbenzylammonium chloride; c) obtaining the at least one fatty acid methyl ester; d) obtaining the at least one viscosity reducing agent; e) obtaining the at least one solubilizing agent; and f) contacting the bis-quaternary ammonium salt of Formula I, alkyldimethylbenzylammonium chloride, the at least one fatty acid methyl ester, the at least one solubilizing agent, and the at least one viscosity reducing agent to obtain the corrosion inhibitor formulation.

In an embodiment of the present disclosure, there is provided a process for the preparation of the corrosion inhibitor formulation comprising: a) the bis-quaternary ammonium salt of Formula I,

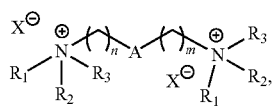

Formula I wherein A is selected from O, NH, S, C(O), C(NH) or C(S); $R_1$ and $R_2$ are independently selected from $C_1$ alkyl or H; $R_3$ is $C_{1-14}$ alkyl; X is chloro; and n and m are independently 1 to 4; b) alkyldimethylbenzylammonium chloride; c) at least one fatty acid methyl ester; d) at least one viscosity reducing agent; and e) at least one solubilizing agent, wherein the bis-quaternary ammonium salt of Formula I to the at least one fatty acid methyl ester weight ratio is in a range of 1:3.7-1:5.7, said process comprising: a) obtaining bis-quaternary ammonium salt of Formula I by the process comprising: i) obtaining at least one alkyl halide; ii) obtaining at least one amine; iii) contacting the at least one alkyl halide and at least one amine in the presence of at least one solvent to obtain the bis-quaternary ammonium salt; b) obtaining the alkyldimethylbenzylammonium chloride; c) obtaining the at least one fatty acid methyl ester; d) obtaining the at least one viscosity reducing agent; e) obtaining the at least one solubilizing agent; and f) contacting the bis-quaternary ammonium salt of Formula I, alkyldimethylbenzylammonium chloride, the at least one fatty acid methyl ester, the at least one solubilizing agent, and the at least one viscosity reducing agent to obtain the corrosion inhibitor formulation.

In an embodiment of the present disclosure, there is provided a process for the preparation of the corrosion inhibitor formulation as described herein, wherein contacting the bis-quaternary ammonium salt of Formula I, alkyldimethylbenzylammonium chloride, the at least one fatty acid methyl ester, the at least one solubilizing agent, and the at least one viscosity reducing agent is carried out at a temperature in a range of 25-70° C. for a period in a range of 10-60 minutes to obtain the corrosion inhibitor formulation. In another embodiment of the present disclosure, contacting the bis-quaternary ammonium salt of Formula I, alkyldimethylbenzylammonium chloride, the at least one fatty acid methyl ester, the at least one solubilizing agent, and the at least one viscosity reducing agent is carried out at a temperature in a range of 50-70° C. for a period in a range of 15-55 minutes to obtain the corrosion inhibitor formulation. In yet another embodiment of the present disclosure, contacting the bis-quaternary ammonium salt of Formula I, alkyldimethylbenzylammonium chloride, the at least one fatty acid methyl ester, the at least one solubilizing agent, and the at least one viscosity reducing agent is carried out at a temperature of 60° C. for a period in a range of 25-45 minutes to obtain the corrosion inhibitor formulation.

In an embodiment of the present disclosure, there is provided a process for the preparation of the corrosion inhibitor formulation as described herein, wherein said process comprising: a) obtaining bis-quaternary ammonium salt of Formula I; b) obtaining the alkyldimethylbenzylammonium chloride; c) obtaining the at least one fatty acid methyl ester; d) obtaining the at least one viscosity reducing agent; e) obtaining the at least one solubilizing agent; and f) contacting the bis-quaternary ammonium salt of Formula I, alkyldimethylbenzylammonium chloride, the at least one fatty acid methyl ester, the at least one solubilizing agent, and the at least one viscosity reducing agent is carried out at a temperature in a range of 25-70° C. for a period in a range of 10-60 minutes to obtain the corrosion inhibitor formulation.

In an embodiment of the present disclosure, there is provided a corrosion inhibitor formulation as described herein, for use in inhibiting corrosion and/or removing hydrocarbonaceous deposits in oil and gas applications.

In an embodiment of the present disclosure, there is provided a corrosion inhibitor formulation as described herein, wherein the corrosion inhibitor formulation is suitable for corrosion prevention of metallurgies comprising carbon steel, copper, brass, lead and zinc involved in fuel pipelines, fuel storage tanks, vehicles fuel tanks during transportation, and fuel distribution systems. In another embodiment of the present disclosure, the metallurgy is carbon steel involved in fuel pipelines.

In an embodiment of the present disclosure, there is provided a corrosion inhibitor formulation as described herein, wherein the corrosion inhibitor formulation has an inhibition efficiency of 97 to 99% for metallurgies selected from the group consisting of carbon steel, copper, mild steel, stainless steel, chromium steel alloys and brass at operating temperature in a range of 0-100° C. In another embodiment of the present disclosure, the corrosion inhibitor formulation has an inhibition efficiency of 97 to 99% for carbon steel at operating temperature in a range of 20-100° C.

In an embodiment of the present disclosure, there is provided a method of inhibiting corrosion comprising: contacting a metallurgy with either the bis-quaternary ammonium salt of Formula I or the corrosion inhibition formulation described herein to obtain a passivated metal. In another embodiment of the present disclosure, said method comprises: contacting a metallurgy with the bis-quaternary ammonium salt of Formula I to obtain a passivated metal. In another embodiment of the present disclosure, said method comprises: contacting a metallurgy with the corrosion inhibition formulation described herein to obtain a passivated metal. In another embodiment of the present disclosure, the metallurgy selected from the group consisting of carbon steel, copper, mild steel, stainless steel, chromium steel alloys and brass.

Although the subject matter has been described in considerable detail with reference to certain preferred embodiments thereof, other embodiments are possible.

EXAMPLES

The disclosure will now be illustrated with working examples, which is intended to illustrate the working of disclosure and not intended to take restrictively to imply any limitations on the scope of the present disclosure. Unless defined otherwise, all technical and scientific terms used herein have the same meaning as commonly understood to one of ordinary skill in the art to which this disclosure belongs. Although methods and materials similar or equivalent to those described herein can be used in the practice of the disclosed methods and compositions, the exemplary methods, devices and materials are described herein. It is to be understood that this disclosure is not limited to particular methods, and experimental conditions described, as such methods and conditions may apply.

As has been mentioned above, corrosion of steel (carbon steel in particular) is a major challenge for the oil and gas industry. Though additive compositions have been attempted, a single composition that is able to provide effective inhibition of corrosion, while being oil soluble is much sought after. In light of same, the present disclosure provides a bis-quaternary ammonium salt of Formula I, wherein the structure has hydrophobic and polar components. The presence of hydrophobic moieties allows the compound to easily disperse in oil. The salt promotes inhibition by typically forming an impenetrable layer over the steel surface. Herein, the bivalent quaternary ammonium salts forms tight bonding and dissociation from the surface is very slow in comparison with the monovalent lipid. Accordingly, the compounds form a very tight layer with the surface, which in turn protect from the corrosion. A formulation comprising the bis-quaternary ammonium salt of Formula I along with a solubilizing agent, a viscosity reducing agent, fatty acid methyl ester and alkyldimethylbenzylammonium chloride is provided that is capable of providing high inhibition efficiency in the range of 97-99%.

Example 1—Process for Obtaining Bis-Quaternary Ammonium Salt (A1)

To a stirred solution of dichloroacetone (at least one alkyl halide) (2 g) in Toluene (at least one solvent) (10 mL), N,N-dimethyldodecylamine or $C_{12}NMe_2$ (at least one amine) (7.4 g) was added at 0° C. and stirred at room temperature for 30 min. The resulting compound was isolated by distillation of the solvent. Yield: 9 g. The LC-MS peaks at 241, 482 confirmed the formation of bis-quaternary ammonium salt (A1).

Example 2—Process for Obtaining Bis-Quaternary Ammonium Salt (A2)

The solution of bisamino propyl ether (1.3 g), benzyl bromide (4 G) in toluene was stirred at 100° C. for 12 h. The resulting compound was isolated by distillation of the solvent. Yield: 4.6 g. The LC-MS data confirmed the disappearance of starting material and formation of the products.

Example 3—Process for Obtaining the Corrosion Formulation (C1)

To a stirred solution of dodecyldimethylbenzylammonium chloride or BKC (4 g), soya bean oil methyl ester (4.7 g) in acetic acid (2.5 g) and isopropanol (0.5 g), quaternary ammonium salt A1 (1 g) was added and heated to temperature of 60° C. for dissolution. The color of the solution slightly changed to blue. The formulation was found to be stable for more than 90 days. In a similar manner the bis-quaternary ammonium salt A2 can be employed to prepare the corrosion inhibitor formulation by replacing A1.

Corrosion inhibition formulation used for carrying out testing have been listed below in Table 1.

| Code | Quaternary ammonium salt A1 | Soya bean oil methyl (FAME) ester | Iso-propyl alcohol (IPA) | Acetic acid (AcOH) | Alkyldimethyl-benzyl-ammonium chloride (50%) |
|---|---|---|---|---|---|
| C1 | 10% | 47% | 0.5% | 2.5% | 40% |
| C2 | 0% | 47% | 0.5% | 2.5% | 50 |

Example 4—Weight Loss Studies

In this study, 5 L of synthetic brine and LVT 200 oil mixture (70:30) was purged with nitrogen (1 hrs), followed by carbon dioxide (2 hrs) to obtain the concentration of oxygen to less than 25 ppb. Subsequently, pre-cleaned and pre-weighed mild steel specimens were suspended in the solution and stirred at a rate of 700 rpm with and without various concentrations of inhibitor formulation C1 (as per Table 1) for a period of 24 hrs. After that, the mild steel specimens were taken out, washed with distilled water, isopropanol, dried with air drier and weighed accurately. The weight loss studies were made in triplicate and the loss of weight was calculated by taking an average (mean) of these values. The standard deviation in the observed weight loss values was calculated and reported. The corrosion rate (CR) is calculated by the following equation (1)—

$$CR = W/St \quad (1)$$

where W is the average (mean value) weight loss of three mild steel specimens, S is the total area of mild steel specimen and t is the immersion time.

From the calculated CR value, the inhibition efficiency (IE %) was calculated according to the following equation (2)—

$$IE(\%) = (Wo - Wi)/(Wo \times 100)$$

where Wo and Wi are the corrosion rate in the absence and presence of various concentrations of corrosion inhibitor, respectively.

20 ppm of the corrosion inhibitor formulation C1, was dosed in a stirred solution of LVT-500 and synthetic brine. The weight loss and corrosion efficiency is shown below in Table 2.

| S. NO | RUN | Corrosion rate (mm/year or mpy) | Inhibition Efficiency (%) |
|---|---|---|---|
| 1 | BLANK | 1.0997 | 0 |
| 2 | REFERENCE | 0.2388 | 78.29 |
| 3 | C1 | 0.0400 | 98.32 |
| 4 | C2 | 0.0411 | 96% |

As can be observed from Table 2, the corrosion inhibitor formulation (C1) performed admirably when compared with commercial product (reference). The inhibition efficiency of reference was found to be 78.29%, whereas a surprisingly high inhibition efficiency of 98.32% was observed for corrosion inhibitor formulation C1.

Advantages Gained in the Example Illustrative Process in this Subject Matter:

The present disclosure reveals bis-quaternary ammonium salts for the preparation of corrosion inhibitor formulations. The valuation of these formulations was performed by weight loss technique. The results indicated that the formulations show excellent corrosion inhibition properties based on their corrosion inhibition efficiency compared to the commercial product. The present disclosure further reveals convenient processes for obtaining the bis-quaternary ammonium salts as well the corrosion inhibitor formulation.

We claim:

1. A corrosion inhibition formulation comprising:
   a) a bis-quaternary ammonium salt of Formula I $$X^- \quad {}^+\!N(R_1)(R_2)-(CH_2)_n-A-(CH_2)_m-{}^+\!N(R_3)(R_1)(R_2) \quad X^- \quad \text{Formula I}$$

wherein A is selected from O, NH, C(O), C(NH) or C(S);
$R_1$ and $R_2$ are independently selected from $C_{1-3}$ alkyl or H; $R_3$ is $C_{1-16}$ alkyl, $C_{13-20}$ aralkyl or $C_{2-16}$ allyl; $X^-$ is selected from chloro, bromo, iodo, hydroxide, nitrate or sulphate; and n and m are independently 1 to 6
b) alkyldimethylbenzylammonium chloride;
c) at least one fatty acid methyl ester;
d) at least one viscosity reducing agent; and
e) at least one solubilizing agent,
wherein the bis-quaternary ammonium salt of Formula I to the at least one fatty acid methyl ester weight ratio is in a range of 1:3.7-1:5.7.

2. The corrosion inhibitor formulation as claimed in claim 1, wherein the bis-quaternary ammonium salt of Formula I to the alkyldimethylbenzylammonium chloride weight ratio is in a range of 1:3-1:5.

3. The corrosion inhibitor formulation as claimed in claim 1, wherein the at least one fatty acid methyl ester is selected from the group consisting of soyabean oil methyl ester, bio-oil derived fatty acid methyl ester, palmitic acid methyl ester, stearic acid methyl ester, oleic acid methyl ester, linoleic acid methyl ester, rapeseed oil methyl ester, and combinations thereof.

4. The corrosion inhibitor formulation as claimed in claim 1, wherein the at least one viscosity reducing agent is selected from the group consisting of isopropanol, propanol, ethanol, toluene, benzene, hexane, kerosene, diesel, propargyl alcohol, and combinations thereof.

5. The corrosion inhibitor formulation as claimed in claim 1, wherein the at least one solubilizing agent is selected from the group consisting of acetic acid, hydroxyacetic acid, tannic acid, 2,6-pyridine dicarboxylic acid, lactic acid, glucono 6-lactone (gluconic acid), 2-puroic acid, thiophene-2-carboxylic acid, 2,3-pyridine dicarboxylic acid, phosphonoacetic acid, thiophene-2-acetic acid, mercapto acetic acid, propionic acid, butanoic acid, pentanoic acid, benzoic acid, and combinations thereof.

6. The corrosion inhibitor formulation as claimed in claim 1, comprises:
a) the bis-quaternary ammonium salt of Formula I wherein A is selected from O, NH, C(O), C(NH) or C(S); $R_1$ and $R_2$ are independently selected from $C_{1-3}$ alkyl or H; $R_3$ is $C_{1-16}$ alkyl, $C_{13-20}$ aralkyl or $C_{2-16}$ allyl; $X^-$ is selected from chloro, bromo, iodo, hydroxide, nitrate or sulphate; and n and m are independently 1 to 6 having a weight percentage in a range of 8-12% with respect to the formulation;
b) alkyldimethylbenzylammonium chloride having a weight percentage in a range of 30-50% with respect to the formulation;
c) at least one fatty acid methyl ester having a weight percentage in a range of 37-57% with respect to the formulation;
d) at least one viscosity reducing agent having a weight percentage in a range of 0.1-0.8% with respect to the formulation; and
e) at least one solubilizing agent having a weight percentage in a range of 1.5-3.5% with respect to the formulation.

7. The corrosion inhibitor formulation as claimed in claim 1, wherein the corrosion inhibitor formulation has a dosage in a range of 10-30 ppm.

8. A process for the preparation of the corrosion inhibitor formulation as claimed in claim 1, said process comprising:
a) obtaining bis-quaternary ammonium salt of Formula I by a process as comprising:
a) i) obtaining at least one alkyl halide;
ii) obtaining at least one amine;
iii) contacting the at least one alkyl halide and at least one amine in the presence of at least one solvent to obtain the bis-quaternary ammonium salt of Formula I;
b) obtaining the alkyldimethylbenzylammonium chloride;
c) obtaining the at least one fatty acid methyl ester;
d) obtaining the at least one viscosity reducing agent;
e) obtaining the at least one solubilizing agent; and
f) contacting the bis-quaternary ammonium salt of Formula I, alkyldimethylbenzylammonium chloride, the at least one fatty acid methyl ester, the at least one solubilizing agent, and the at least one viscosity reducing agent to obtain the corrosion inhibitor formulation.

9. A process for preparing the corrosion inhibitor formulation as claimed in claim 8, wherein contacting the bis-quaternary ammonium salt of Formula I, alkyldimethylbenzylammonium chloride, the at least one fatty acid methyl ester, the at least one solubilizing agent, and the at least one viscosity reducing agent is carried out at a temperature in a range of 25-70° C. for a period in a range of 10-60 minutes to obtain the corrosion inhibitor formulation.

10. The corrosion inhibitor formulation as claimed in claim 1, wherein the corrosion inhibitor formulation is characterized to inhibit corrosion and/or remove hydrocarbonaceous deposits in oil and gas applications.

11. The corrosion inhibitor formulation as claimed in claim 10, wherein the corrosion inhibitor formulation is characterized to prevent corrosion of metallurgies comprising carbon steel, copper, brass, lead and zinc involved in fuel pipelines, fuel storage tanks, vehicles fuel tanks during transportation, and fuel distribution systems.

12. The corrosion inhibitor formulation as claimed in claim 11, wherein the corrosion inhibitor formulation has an inhibition efficiency of 97 to 99% for metallurgies selected from the group consisting of carbon steel, copper, mild steel, stainless steel, chromium steel alloys and brass, at an operating temperature in a range of 0-100° C.

* * * * *